United States Patent [19]

Malenchek

[11] Patent Number: 5,478,314
[45] Date of Patent: Dec. 26, 1995

[54] NON-REUSABLE SYRINGE

[76] Inventor: Robert Malenchek, 279 Sunnymead Rd., Somerville, N.J. 08876

[21] Appl. No.: 364,742

[22] Filed: Dec. 27, 1994

[51] Int. Cl.⁶ .................................................. A61M 5/00
[52] U.S. Cl. ......................... 604/110; 604/220; 604/228
[58] Field of Search .................................. 604/110, 187, 604/220, 218, 228

[56] References Cited

U.S. PATENT DOCUMENTS

| | | | |
|---|---|---|---|
| 4,923,443 | 5/1990 | Greenwood et al. | 604/228 X |
| 4,973,308 | 11/1990 | Borras et al. | 604/110 |
| 4,973,309 | 11/1990 | Sultan | 604/228 X |
| 5,090,962 | 2/1992 | Landry, Jr. et al. | 604/220 X |
| 5,181,912 | 1/1993 | Hammett | 604/110 |
| 5,195,975 | 3/1993 | Castagna | 604/110 |
| 5,328,484 | 7/1994 | Somers et al. | 604/110 X |

*Primary Examiner*—John D. Yasko
*Attorney, Agent, or Firm*—Omri M. Behr; Matthew J. McDonald

[57] ABSTRACT

A syringe tubular body forms a fluid receiving chamber having a restricted opening at one end for receiving a hollow needle and a wider opening at the other end for receiving a tubular plunger. The plunger has resilient fingers at its distal end which is inserted into the body chamber and an annular groove in one embodiment adjacent the proximal end. The fingers have inwardly extending hook-like projections. A piston assembly includes a body with an annular groove which releasably receives the projections for securing the piston assembly to the plunger during injection, the piston assembly including an elastomeric disc piston sealingly engaged with the tubular body chamber sides. A sleeve is external and movable along the body and is next adjacent the disc. The sleeve has an annular groove which is selectively engaged by the projections. The sleeve has an axial extent greater than that of the piston assembly body groove. When the piston is fully inserted into the chamber during injection, further displacement forces the disc piston against the chamber bottom permitting the finger projections to be forced out of engagement with the piston assembly body groove and into locking engagement with the sleeve groove, or in the alternative, to break away. When the plunger is withdrawn from the chamber, the engaged sleeve is withdrawn therewith and precludes the projections from engaging the piston assembly body groove leaving the piston in the chamber to preclude further use of the syringe tubular body. When the projections break, the piston is also left in the body chamber.

18 Claims, 6 Drawing Sheets

FIG. 10

NON-REUSABLE SYRINGE

FIELD OF THE INVENTION

This invention relates to syringes, and particular, to syringes which can be used only one time.

SUMMARY OF THE INVENTION

A non-reusable syringe device according to the present invention comprises a first cylindrical body having a chamber defined by at least one side wall, the body having a first opening at a proximal end of the body and a second opening at an end of the body distal the proximal end, the openings being in communication with the chamber, the second opening for receiving a hollow core needle. Plunger means are included for insertion through first opening into the chamber for injecting a fluid through the second opening in response to displacement of the plunger means in the chamber. Piston means detachably secured to the plunger means are selectively releasable in the chamber for preventing flow of fluid through said second opening from said chamber.

In one embodiment, the piston means comprises an elastomeric disc in fluid sealingly engagement with the at least one side wall.

In a further embodiment, the plunger means includes a plunger having at least one radially inwardly extending opposing pair of projections each having an inclined surface facing away from the distal end, the piston means including a second body having opposing recesses each releasably engaged with a different projection so that the second body displaces with the plunger during the displacement of the plunger.

Means are provided for securing the piston means to the second body so the piston means displaces with the plunger, and a sleeve member is movably secured over the second body and has at least one second recess for selective engagement with a different projection.

The member is arranged such that the inclined surfaces of the projections engage the member in response to further axial displacement of the plunger toward the first body distal end and cause the projections to engage the second recesses, the piston means being larger than the second opening such that the first body resists the further displacement of the piston means whereby the projections resiliently disengage from the first recesses into engagement with the second recesses during the further displacement.

DISCUSSION OF THE PREFERRED EMBODIMENTS

Figure 1:
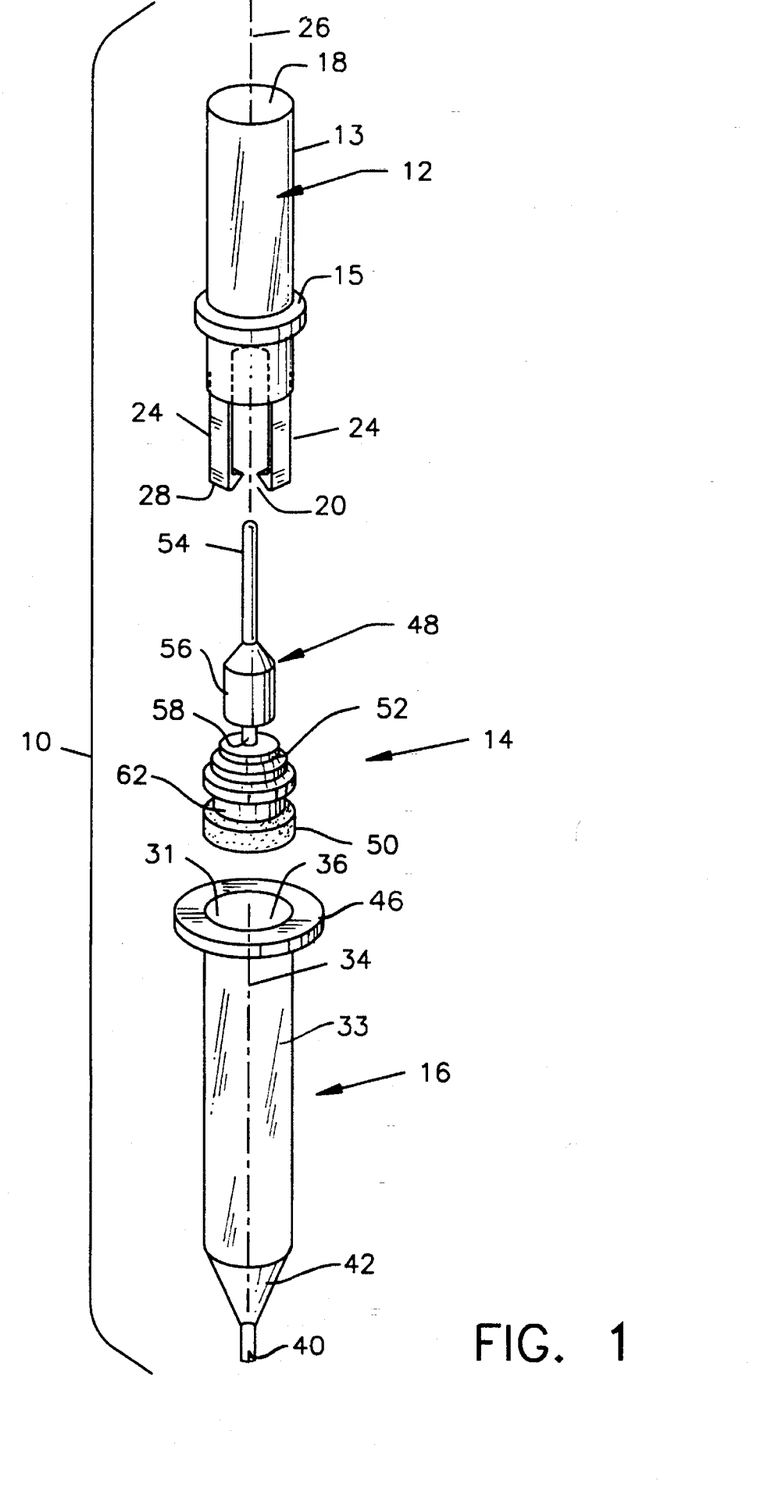
FIG. 1 is an isometric exploded view of an embodiment of the present invention.

In FIG. 1, syringe 10 includes a plunger 12, a piston assembly 14 and a syringe body 16. The plunger 12 is a preferably molded thermoplastic circular cylindrical tube 13, initially open at proximal end 18 and also open at the opposite distal end 20, the plunger having a bore 22, FIG. 2, concentric with axis 26. The opening at end 18 may be closed later with a plug (not shown) if desired to provide a finished appearance to the plunger.

Figure 3:
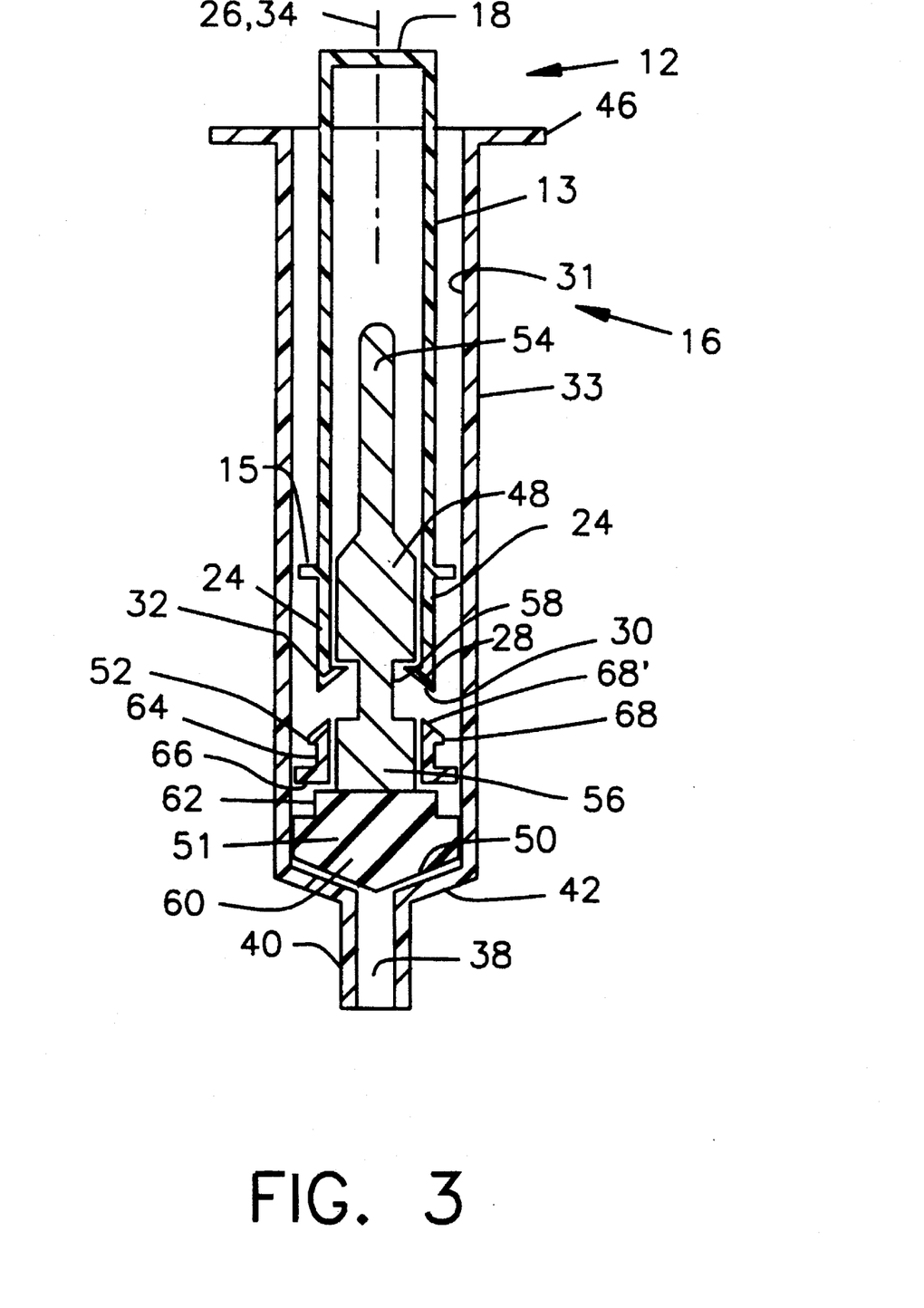
FIG. 3 is a side elevation sectional view of the device of FIG. 2 showing the device with the plunger in its position after just completing a first use injection.

The plunger 12 tube 33 end 20 is formed with an annular array of, preferably four, equally spaced axially extending cantilevered fingers 24 which are radially resilient in a direction normal to axis 26 of bore 22. Only two of the fingers are shown in FIG. 1, the fingers being arranged in opposing pairs. Each finger is formed with a radially inwardly extending projection 28 at its tip. The projections of the opposing pairs face one another. The projection 28 is identical on each finger. The projection 28 has a surface 30 which is inclined toward axis 26 to form a ramp. As best seen in FIG. 3, the projection 28 has a planar surface 32 extending beyond the body of the finger 24 normal to the axis 26 forming a hook. An annular radially outwardly extending outer flange 15 extends about the medial section of the tube 13.

Figure 2:
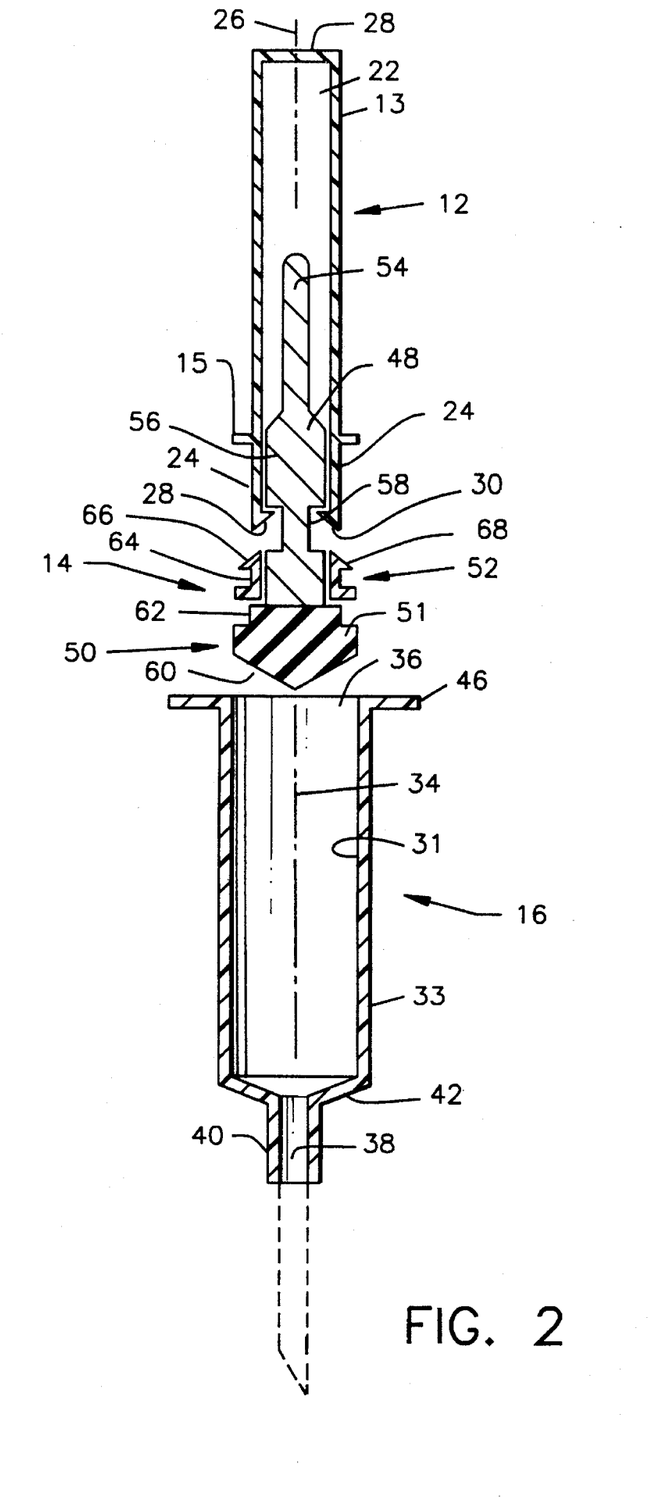
FIG. 2 is an exploded side elevation sectional view of the device of FIG. 1 partially assembled prior to use.

The syringe body 16, FIG. 2, is a preferably thermoplastic molded tube 33 having an elongated, preferably circular cylindrical, chamber 31 concentric with axis 34. The proximal end of the tube 33 has an opening 36 for receiving the plunger 12 therethrough into the chamber 31 with the axes 26 and 34 substantially coaxial. The plunger 12 is thus nested with the tube 33 in the chamber 31 when inserted therein. The body 16 has an opening 38 of restricted diameter relative to opening 36 at the tube 33 end distal the opening 36, FIG. 2. The opening 38 is formed in conical bottom wall 42 and continues in a tubular extension 40 lying on axis 34 and extending beyond the conical bottom wall 42. Extension 40 is an extension of the tube 33 and is integral therewith. The extension 40 is dimensioned to receive a hollow needle 44, shown in phantom in FIG. 2 for purposes of injecting through the needle a fluid (not shown) in the chamber 31 in response to axial displacement of the plunger in a known way. The body 16 includes an annular flange 46 for grasping during injection.

The piston assembly 14, FIG. 2, includes a body member 48, an elastomeric piston 50 secured to the member 48 by any suitable fastening devices such as bonding by adhesive or other fastening arrangements and a sleeve 52. The body member 48 comprises, FIG. 3, optionally an upstanding cylindrical extension 54 and a circular cylindrical portion 56 which is closely received in the bore 22 of plunger 12 on axis 26. The extension 54 is of smaller diameter than portion 56. Portion 56 is formed with an annular groove 58 forming a channel whose sides lie in parallel planes parallel to the projection 28 surfaces 32, normal to axis 26. The piston 50 is secured to the end surface of the portion 56.

The piston 50 includes an elastomeric disc 51 with a depending conical bottom portion 60 which matches the contour of the tube 33 bottom wall 42 in chamber 31. The piston 50 also has an upstanding circular cylindrical member 62 of smaller diameter than and which is integral with the disc 51 forming a one piece homogeneous structure. Disc 51 has an outer diameter larger than the inner diameter dimension of the tube 33 chamber 31 to compressively engage-the sidewall of chamber 31 in fluid sealingly engagement.

In FIG. 3, preferably molded thermoplastic, sleeve 52 comprises a circular cylindrical tube-like member with an annular groove 64 formed by spaced annular rib 66 and hook-like rib 68. Rib 68 has an inclined face 68' that faces the inclined surfaces 30 of projections 28 on fingers 24. The inclination of the surfaces 68' and 30 are the same and preferably about 45° to axes 26, 34.

Figure 8:
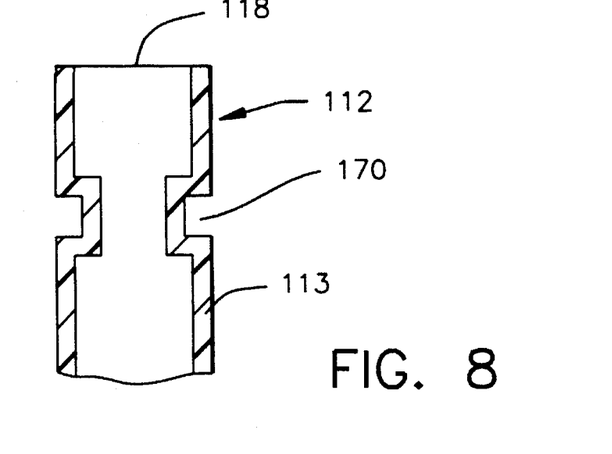
FIG. 8 is a sectional elevation fragmented view of an end region of a plunger according to a second embodiment of the present invention.

In a further embodiment shown in FIG. 8, plunger 112 is formed with a groove 170, preferably annular [groove], [is placed] in wall 113 proximate to the plunger 112 end 118. A clip 172, illustrated in FIG. 9, preferably molded thermoplastic, has slot 174 and a pair of opposing like flanges 176 in the slot 174. The space between the flanges 176 is dimensioned to releasably and slidably fit snugly into groove 170. The groove 170, FIG. 10, is so located along the length of the plunger 112 such that when plunger 112 is in the position shown for plunger 12 in FIG. 3, clip 172 body portion 178 rests on top of annular flange 46, thus preventing further downward travel of plunger 112.

In operation, the piston assembly 14 is first assembled to the plunger 12 by inserting the body 48 into the tube 13 bore 22, FIG. 2, until the projections 28 on fingers 24 engage the groove 58 in the body 16. This releasably secures the piston assembly 14 to the plunger 12 as shown in FIG. 2. Then the plunger 12 with the piston assembly 14 is inserted into the open proximal opening 36 of the tube 33 into chamber 31 in the axial direction of axes 26, 34. The plunger and piston assembly is fully inserted to the position shown in FIG. 3. In this position the piston conical portion 60 is close to or abuts the tube 33 bottom wall 42 in chamber 31. The disc 51 remains sealed against the chamber sides in this position.

Two modes of assembly should be considered. In automatic assembly the [combined] plunger 12/piston 14 combination is held on an insertion tube, not shown, into which extension 54 fits. A downward insertion force is then exerted solely upon piston assembly 14. This also inserts the plunger since the plunger is secured to the piston assembly 14 via the projections 28 engaged in groove 58. In this way, there is no possibility of plunger 12 traveling downwardly relative to the piston assembly 14 during insertion. If such relative motion were permitted to occur, when the piston assembly abuts the bottom wall 42 of tube 33, [so that] fingers 28 will flex radially outwardly and ride over inclined surface 68' of rib 68 and engage and lock to the sleeve 52 groove 64. This is undesirable at this time because the piston assembly 14 is prematurely released from the plunger 12 as will be explained below.

Figure 9:
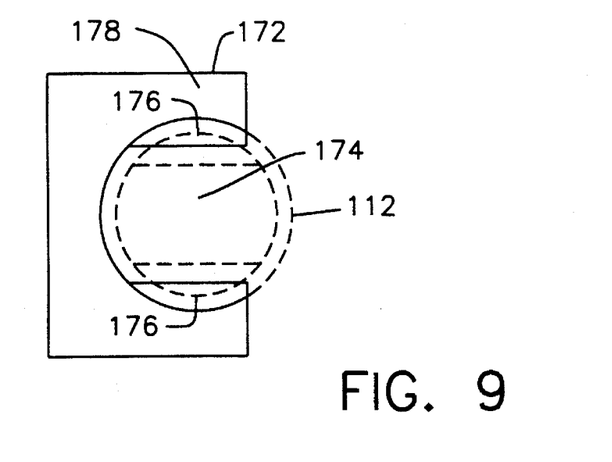
FIG. 9 is a plan view of a clip for attachment to the plunger of FIG. 8 shown in phantom in FIG. 9.
Figure 10:
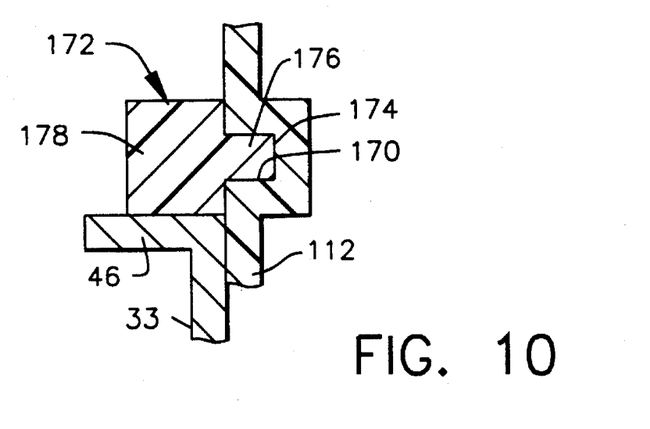
FIG. 10 is a side elevation fragmented sectional view of the plunger of FIG. 8 with the clip of FIG. 9 releasably attached thereto.

In manual assembly, in the embodiment of FIGS. 8, 9 and 10 [and 9], clip 172 is inserted into groove 170 on plunger 112. The clip 172 when it abuts the flange 46 precludes further downward displacement of the plunger and piston assembly. This stoppage of further downward displacement of the plunger occurs before the plunger is permitted to displace relative to the sleeve 52 and piston 50 at the time the piston 50 abuts the bottom wall 42. This action avoids the riding of fingers 28 over inclined rib 68, because of excessive assembly pressure on plunger 112 relative to the sleeve 52.

The syringe is then loaded by inserting the needle, FIG. 2, into a fluid, e.g., liquid, filled container (not shown). Plunger 12 is then drawn upwardly, such as in direction 72, FIG. 5, whereby disc 51 being substantially sealed to the inner surface of tube 33 forms a pressure less than atmospheric therein, causing the liquid to travel into the space formed by the upward movement of the plunger 12. If clip 172 is present, it should then be removed. The syringe is now ready to inject the liquid medium into [the] a patient.

Figure 4:
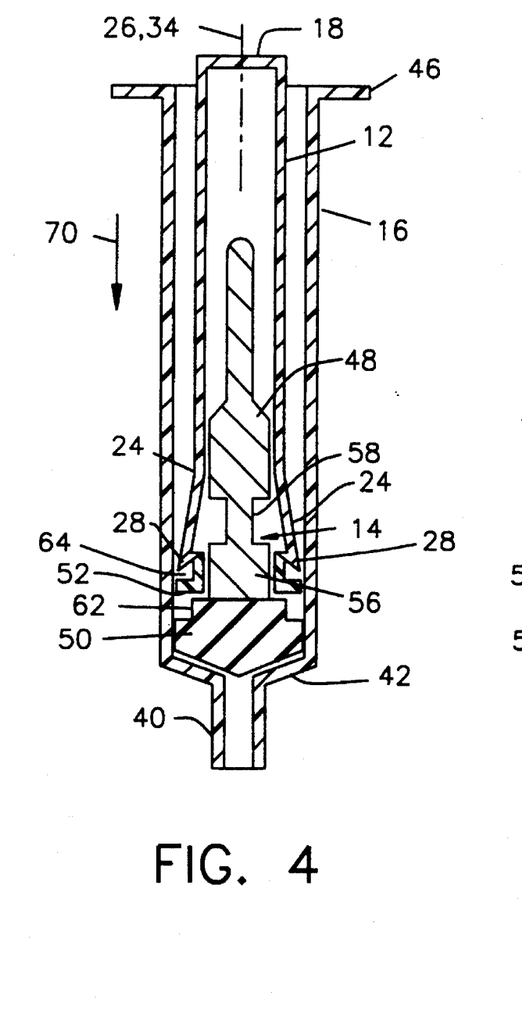
FIGS. 4 and 5 are side elevation sectional views of the device of FIG. 3 showing further axial displacements of the plunger as it disengages the piston portion.

This injection occurs in the conventional manner wherein the plunger 12 is displaced in direction 70, FIG. 4. The plunger 12 is then displaced further in direction 70 while the piston 50 abuts the bottom wall 42. This causes the projections 28 to ramp out of the body 48 groove 58 against the inclined face 68' of rib 68 of sleeve 52. This is a detent action. The inclined faces 30 of the projections 28 ramp the projections out of the groove 58 because the inclined faces 30 of projections 28 extend out of the groove 58 in the normal mode when locked to the body 48, FIG. 2, and thus can engage the inclined faces 68' of rib 68.

Figure 5:
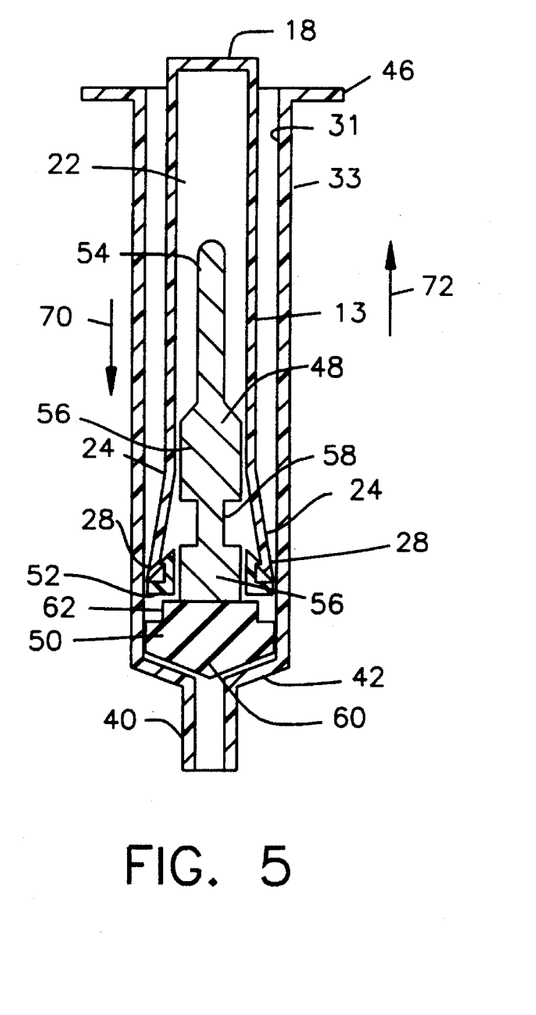

Continuing further axial displacement in direction 70 causes the projections to snap into the sleeve 52 groove 64, FIG. 5. At this time, the planar hook-like surfaces normal to axis 26 of the projections 28 engage the planar side normal to axis 26 of hook-like rib 68 in groove 64 of sleeve 52. This locks the projections 28 to the sleeve 52.

Figure 6:
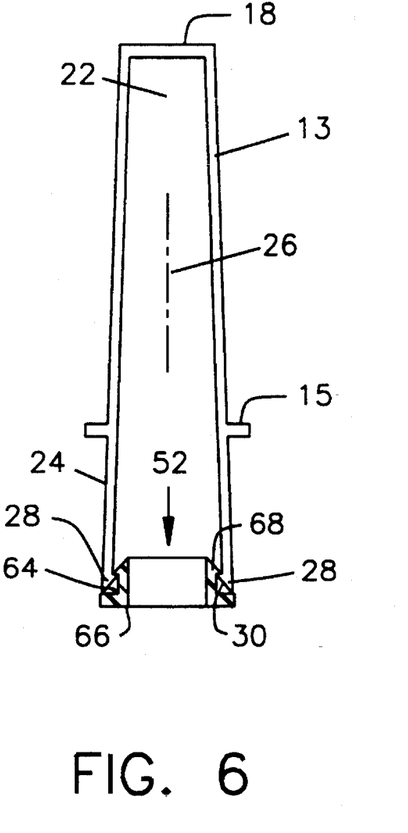
FIG. 6 is a side elevation sectional view of the plunger after it has been withdrawn from the syringe body.
Figure 7:
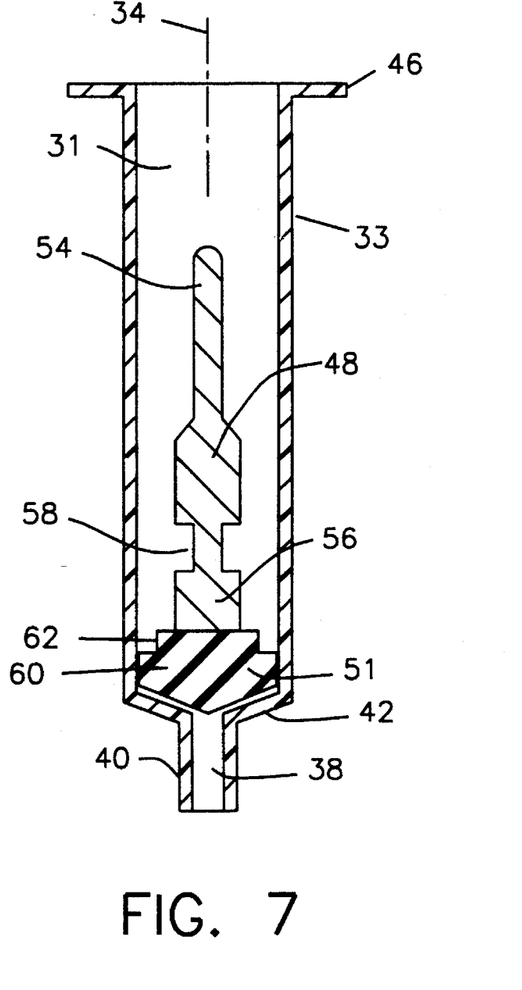
FIG. 7 is a side elevation sectional view of the syringe body with its needle opening blocked by the released plunger piston to preclude further use of the syringe.

The sleeve 52 has an axial extent in direction 70 that is greater than the axial extent of body 16 groove 58. This is important. If desired, plunger 12 may be withdrawn from chamber 31 in direction 72, FIG. 5. The projections 28 are locked to the sleeve 52 via the sleeve groove 64, and this locked engagement pulls the sleeve with the plunger in direction 72 out of the chamber 31. The plunger and engaged sleeve 52 out of chamber 31 are shown in FIG. 6. This action leaves the piston assembly 14 in the chamber 31 as shown in FIG. 7. In this position, the piston disc 50 seals the chamber 31 blocking The discharge bore 38. Thus, no liquid can be injected from the chamber 31 into the bore 38 at the bottom of the chamber 31 in this mode. Thus the syringe can not be reused. The plunger 12 is thus selectively displaced to disengage it from the piston assembly releasably secured to the plunger.

In an alternative embodiment, [piston] plunger 12 is molded from a readily fractable plastic such as polystyrene. When projections 28 ride over rib 68, they do not engage in groove 64, but break [off] such that the piston assembly is no longer attached to the plunger 12. Thus, piston assembly 14 is immobilized in chamber 31 when the plunger 12 is withdrawn from the body 16 and the syringe is again unusable. The collar 15 prevents spillage of the severed projections 28 from the chamber 31 to the ambient atmosphere.

While a particular embodiment has been disclosed herein, it will occur to those of ordinary skill that modifications can be made thereto. It is intended that the scope of the invention is as defined in the appended claims. For example, other devices may used to seal the chamber from reuse including a separate piston device that is inserted in response to the insertion of the plunger, but: not attached to the plunger. However, it is preferred that the piston device be attached to the plunger and released therefrom to provide a single step to preclude reuse.

What is claimed is:

1. A non-reusable syringe device comprising:

a first cylindrical body having a chamber defined by at least one side wall, the body having a first opening at a proximal end of the body and a second opening at an end of the body distal the proximal end, the openings being in communication with the chamber, the second opening for receiving a hollow core needle;

plunger means for insertion through first opening into the chamber for injecting a fluid through the second opening in response to displacement of the plunger means in said chamber in an injection direction, said plunger means including resilient projection means;

fluid blocking means selectively insertable into said chamber for preventing flow of fluid through said second opening in response to said plunger means displacement, said fluid blocking means including piston means in fluid sealingly contact with said at least one side wall for precluding fluid flow past the piston means from the proximal end to the distal end, said piston means having a first recess selectively engaged with said projection means to couple the piston means to the plunger for said injecting in said injection direction; and piston decoupling means for selectively decoupling the fluid blocking and piston means from the plunger upon completion of said injecting, said decoupling means comprising a sleeve movably secured to the fluid blocking means for selectively moving over and disabling said first recess relative to said projection means, said decoupling means having a second recess for selectively receiving and engaging said resilient projection means upon further displacement of the plunger means in the injection direction upon completion of the injecting to couple the sleeve to the plunger means and decouple the projection means from the first recess so that upon withdrawal of the plunger means said sleeve disengages from said piston means to thereby selectively insert the fluid blocking means in said chamber.

2. The device of claim 1 wherein the piston means includes an elastomeric disc in fluid sealingly engagement with the at least one side wall.

3. The device of claim 1 wherein the piston means is arranged to be spaced adjacent to said second opening distal said proximal end when released to preclude manual retrieval of the piston means from the chamber.

4. The device of claim 1 wherein the blocking means includes a second body .having said first recess so as to be releasably attached to the plunger means, said piston means including a piston member attached to the second body in said fluid sealingly engagement with the chamber at least one side wall, said plunger means including a plunger having proximal and distal ends, the plunger proximal end being adjacent to the first body proximal end upon completion of said injecting, said second body being releasably attached to the plunger by said projection means and first recess at the plunger distal end.

5. The device of claim 4 wherein the plunger has a bore extending in an axial direction, said projection means and first recess for releasably securing the second body in said bore and said piston member outside said bore at said plunger distal end.

6. The device of claim 5 wherein the chamber extends in said axial direction from the proximal to distal body ends, the piston means being larger in transverse dimension than said second opening for resisting the further axial displacement of the plunger beyond the first body distal end, the first resilient projection means comprises at least one finger formed in the plunger and being radially inwardly flexible relative to said axial direction, said finger including a radially inwardly extending projection at said plunger distal end, said first recess in the second body for receiving the projection to releasably secure the second body and piston means to the plunger, said second recess for selectively receiving said projection, said projection and recesses being arranged such that axial displacement of the plunger toward said first body distal end is such that the piston means displacement is resisted by said first body and disengages the projection from the first recess and engages the projection with the second recess such that axial withdrawal of the plunger toward said body proximal end causes said sleeve and projection to displace past said first recess releasing the piston in said chamber.

7. A selectively non-reusable syringe device comprising:

a first cylindrical body having a chamber defined by at least one side wall and extending along an axis, a first opening at a proximal end of the body and a second opening at an end of the body distal the proximal end, the openings being in communication with the chamber along the chamber axis, the second opening for receiving a hollow core needle along said axis;

a plunger having proximal and distal ends for axial insertion of the distal end through first opening into the chamber; and piston means having opposing sides and selectively releasably attached to the plunger distal end for forcing a fluid through said second opening in response to axial displacement of the plunger and for selective release from the plunger while in said chamber after said displacement, said piston means being configured to prevent fluid flow from a side of the piston means facing the first opening to the other side facing said second opening when released in said chamber;

said plunger having a radially inwardly-extending projection at said plunger distal end, said piston means comprising a second body having a first recess therein for releasably receiving said projection, a piston member secured to the second body at said plunger distal end in fluid sealingly engagement with said at least one side wall, and a sleeve member movably secured over said second body arranged to displace over and disable the first recess relative to said projection, said sleeve having a second recess therein for selective engagement with said projection disengaged with the first recess such that further displacement of the plunger toward said second opening causes the projection to disengage from the first recess and engage the second recess to secure the sleeve member thereto such that withdrawal of the plunger from the chamber removes the sleeve from the chamber therewith while causing said second body and piston means to remain in said chamber.

8. The device of claim 7 wherein the first body and the plunger each comprise a cylindrical thermoplastic tube and wherein the plunger has a bore for receiving the second body.

9. The device of claim 8 wherein the plunger has a radially inwardly extending opposing pair of said projections each having an inclined surface facing away from said distal end, said second body having opposing recesses each releasably engaged with a different projection so that the second body displaces with the plunger during said displacement of the plunger, at least one of said second recess for selective engagement with a different projection, said sleeve member being arranged such that the inclined surfaces of the projections engage the sleeve member in response to further axial displacement of the plunger toward said first body distal end and cause the projections to engage the second recesses, said piston means being larger than said second opening such that the first body resists said further displacement of the piston means whereby the projections resiliently disengage from the first recesses into engagement with the second recesses during said further displacement.

10. The device of claim 9 wherein the sleeve member has an axial extent greater than that of the first recesses so that upon withdrawal of the plunger from said first opening, the projections engaged with the sleeve member ride over the first recesses to thereby release the second body and piston means from the plunger.

11. The device of claim 9 wherein the at least one second recess is an annular groove.

12. The device of claim 9 wherein the sleeve member has at least one inclined surface which faces and is arranged to engage the inclined surfaces of said projections during said further displacement.

13. The device of claim 9 wherein the plunger and first body are circular cylindrical, said second body having a first portion located in said plunger bore and a second portion extending beyond the bore, said sleeve member being concentric with said second portion and substantially coextensive with said plunger in the axial direction at said plunger distal end.

14. The device of claim 13 wherein the piston means comprises an elastomeric disc secured to the second body adjacent to said sleeve member distal said plunger.

15. The device of claim 7 wherein the piston means abuts the body at the distal end after said displacement, the means for selective release of the piston means including means coupled to the piston means and plunger responsive to further axial displacement of the plunger upon said abutting for release of said piston means.

16. The device of claim 15 including detent means coupled to the plunger means and piston means for selectively releasing the piston means from the plunger.

17. The device of claim 16 including clip means releasably secured to the plunger for selectively precluding said further axial displacement.

18. The device of claim 17 wherein the clip means includes a clip with a slot and opposing flanges and an annular groove in the plunger for receiving the opposing flanges.

\* \* \* \* \*